United States Patent
Davis

(10) Patent No.: US 8,747,770 B2
(45) Date of Patent: *Jun. 10, 2014

(54) MOBILE UV STERILIZATION UNIT FOR FIELDS AND METHOD THEREOF

(75) Inventor: Michael E. Davis, Brownsburg, IN (US)

(73) Assignee: GreenZapr, Inc., Indianapolis, IN (US)

( * ) Notice: Subject to any disclaimer, the term of this patent is extended or adjusted under 35 U.S.C. 154(b) by 669 days.

This patent is subject to a terminal disclaimer.

(21) Appl. No.: 12/966,232

(22) Filed: Dec. 13, 2010

(65) Prior Publication Data

US 2011/0274582 A1 Nov. 10, 2011

Related U.S. Application Data

(63) Continuation-in-part of application No. 12/775,515, filed on May 7, 2010, now Pat. No. 8,506,897.

(51) Int. Cl.
*B01J 19/00* (2006.01)
*A61L 2/00* (2006.01)

(52) U.S. Cl.
USPC .............................................. 422/291; 422/24

(58) Field of Classification Search
USPC ................................................... 422/24, 291
See application file for complete search history.

(56) References Cited

U.S. PATENT DOCUMENTS

| | | | |
|---|---|---|---|
| 3,633,679 A | 1/1972 | Dahlberg et al. | |
| 5,902,552 A | 5/1999 | Brickley | |
| 5,968,455 A | 10/1999 | Brickley | |
| 7,459,694 B2 | 12/2008 | Scheir et al. | |
| 7,476,885 B2 * | 1/2009 | Garcia et al. | 250/504 H |
| 8,112,841 B2 * | 2/2012 | Garcia et al. | 15/319 |
| 2002/0139355 A1 | 10/2002 | Gracyalny et al. | |
| 2003/0159840 A1 | 8/2003 | Schmidt | |
| 2008/0295271 A1 | 12/2008 | Perunicic | |
| 2010/0104471 A1 | 4/2010 | Harmon et al. | |

FOREIGN PATENT DOCUMENTS

| | | |
|---|---|---|
| JP | 09239352 A | 9/1997 |
| KR | 2001070293 | 7/2001 |
| KR | 2003053596 | 7/2003 |
| KR | 2003080226 | 10/2003 |
| KR | 2004007560 | 1/2004 |
| KR | 518620 | 10/2005 |

* cited by examiner

*Primary Examiner* — Kevin Joyner
(74) *Attorney, Agent, or Firm* — Woodard, Emhart, Moriarty, McNett & Henry LLP

(57) ABSTRACT

A mobile ultraviolet sterilization vehicle. A plurality of UV lamps are removably mounted to a wheeled vehicle. A plurality of tines and a brush are mounted to the vehicle extending across the width thereof and into the supporting surface to position the supporting surface to receive the UV light.

5 Claims, 13 Drawing Sheets

MOBILE UV STERILIZATION UNIT FOR FIELDS AND METHOD THEREOF

This application is a continuation-in-part of U.S. patent application Ser. No. 12/775,515, filed May 7, 2010, now U.S. Pat. No. 8,506,897.

BACKGROUND OF THE INVENTION

1. Field of the Invention

The present invention is in the field of apparatus for sterilizing fields and more specifically sports fields.

2. Description of the Prior Art

High-performance, artificial athletic fields are increasingly being installed and used in communities. Many of these fields are "infill turf systems" in which blades of synthetic grass are tucked into a backing system that is covered with a deep layer of sand and/or synthetic particles (the infill material). The infill materials are often made of small particles of rubber or plastic, which fills the spaces between the fibers (blades of "grass") to hold the fibers up and to provide a cushion surface.

The infill material and synthetic fibers can provide a host for a variety of substances including mold, bacteria and a variety of germicidal agents. The current procedure is to spray various chemicals on the field to thereby sterilize the field and provide a safe environment. Spraying of chemicals onto artificial fields is quite expensive due not only to the labor involved but also the cost of raw materials.

An alternate approach in decontaminating surfaces is through the use of ultraviolet light. For example, In U.S. Pat. No. 7,459,694, there is disclosed a mobile germicidal system for decontaminating walls and a ceiling of a room. Germicidal lamps are positioned adjacent the wall and/or ceiling to thereby sterilize the surface. U.S. Pat. No. 5,902,552 discloses an ultraviolet air sterilization device for connection to an air handling duct for the purpose of sterilizing the air as it flows through the duct. U.S. Pat. No. 5,968,455 discloses a mobile unit incorporating many of the features of U.S. Pat. No. 5,902,552 and includes a wheeled carriage with a handle to allow the operator to traverse the sterilization device over a floor covering.

Despite the prior devices and the availability of germicidal lamps and associated fixtures, there is still a need for a mobile device that is easily movable across a field such as a synthetic soccer or football field for quickly destroying undesirable agents existing on the synthetic field. Further, since the synthetic fibers have embedded therebetween loose infield material, simply passing a UV light over the field may not maximize the sterilization. Thus, there is a further need to have on the vehicle infill material devices for moving and turning over the infill material thereby exposing the infill material to the sterilization lamps.

The so called "green effect" is the characteristic of a machine, method, etc. to achieve a desired result with the least impact on the environment. There is a need to have an aforementioned mobile UV sterilization apparatus that is battery powered that is rechargeable once the energy is depleted. Disclosed herein is an apparatus and method which fulfills all of the aforementioned needs.

SUMMARY OF THE INVENTION

One embodiment of the present invention is a method of minimizing infectious material on blades of a turf field comprising the steps of providing a vehicle having downwardly shining ultraviolet lamps spaced apart from blades of a turf field, further, spacing the lamps apart from the field a first distance to minimize infectious material thereon, moving the vehicle across the turf field in a first direction while the lamps shine ultraviolet energy against first portions of the blades of the turf field, and moving the vehicle across the turf field in a second direction different from the first direction while the lamps shine ultraviolet energy against second portions of the blades of the turf field.

Another embodiment of the present invention is a vehicle to move across a sports field having blades to destroy infectious material on the field comprising a frame, a wheel rotatably mounted on the frame and extending downwardly to support the frame, a source of ultraviolet light mounted on the frame and having ultraviolet lamps to shine downwardly against the field, a source of electrical energy mounted on the frame and connected to the ultraviolet lamps and an engager mounted on the frame forwardly of the source of ultraviolet light that extends down contacting and positioning the blades on the field to receive the ultraviolet light.

It is an object of the present invention to provide a new method and apparatus for sterilizing sports fields.

A further object of the present invention is to provide a mobile ultraviolet sterilization vehicle that will maximize the sterilization of a sports field.

Yet a further object of the present invention is to provide an ultraviolet sterilization vehicle designed to have minimum impact on the environment.

An additional object of the present invention is to provide a method of minimizing infectious material on blades of a turf field wherein ultraviolet light is direct against the blades as the source of the ultraviolet light is moved in different directions across the field.

Related objects and advantages of the present invention will be apparent from the following description.

DESCRIPTION OF THE PREFERRED EMBODIMENTS

Figure 1:
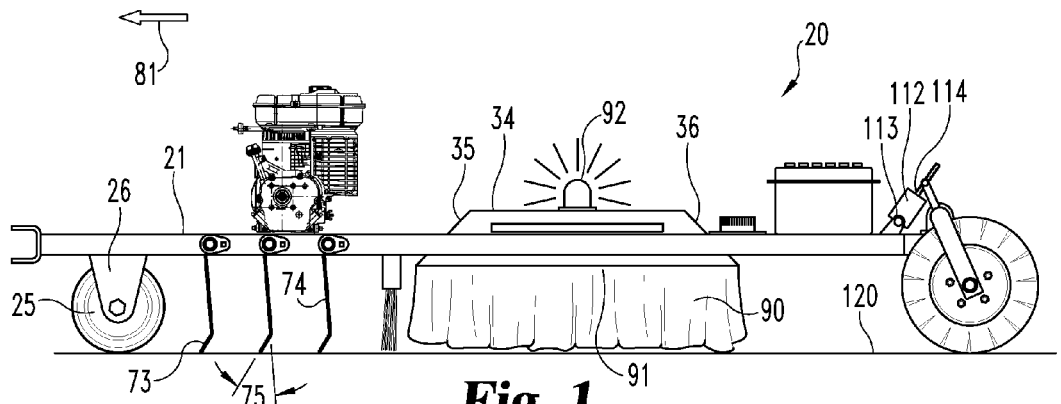
FIG. 1 is side view of an alternate embodiment of the mobile vehicle incorporating the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
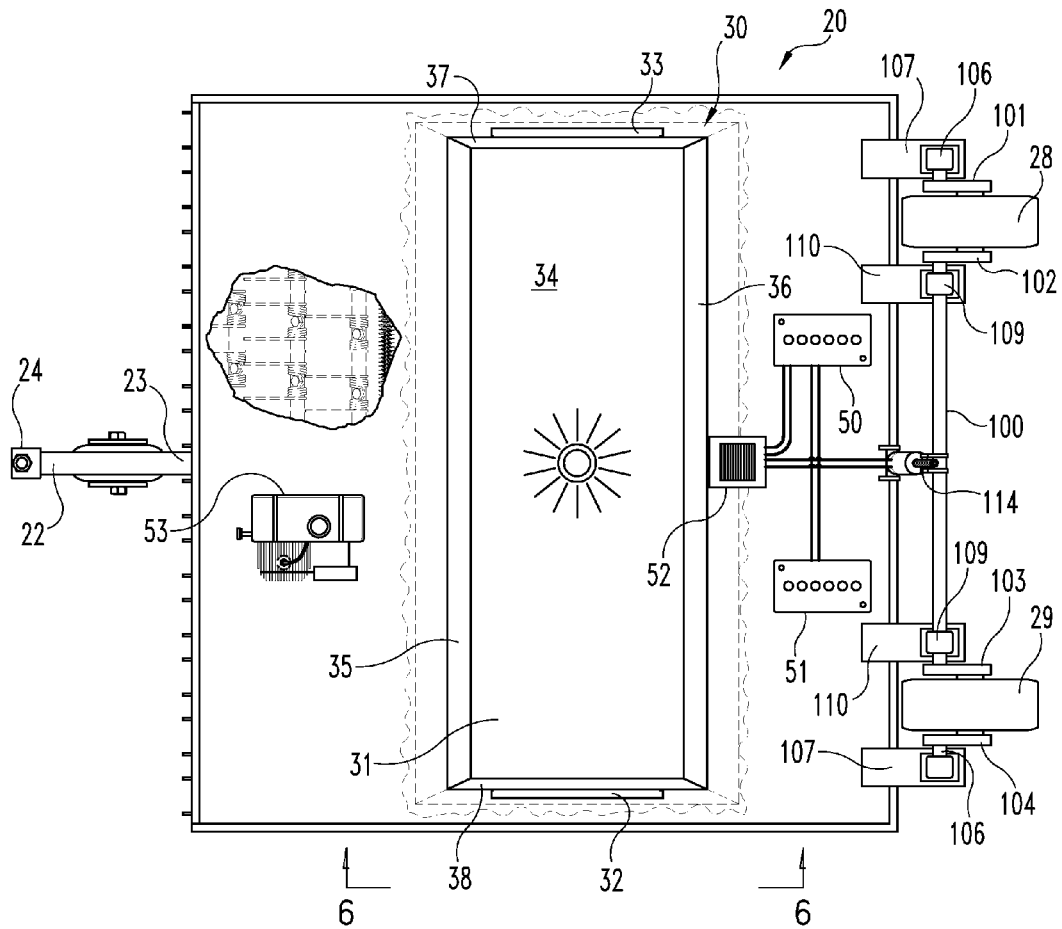
FIG. 2 is a fragmentary top view of the vehicle of FIG. 1.
Figure 3:
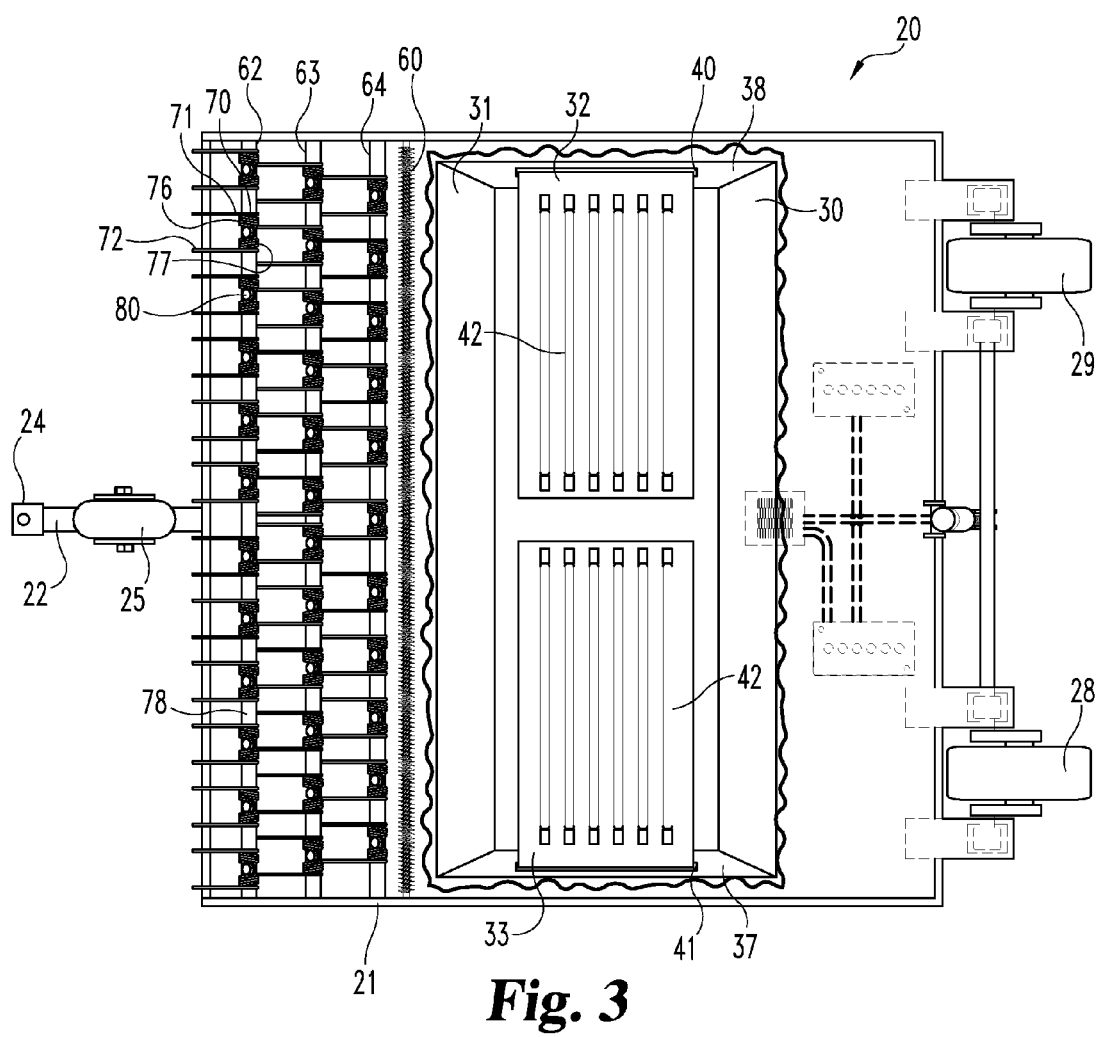
FIG. 3 is a bottom view of the vehicle of FIG. 1.

Referring now more particularly to FIGS. 1-3, there is shown the alternate embodiment of a mobile vehicle 20 incorporating the present invention having a main frame 21 with a general rectangular configuration. A tow bar 22 has a proximal end 23 fixedly mounted to frame 21 and a distal end 24 forming a conventional hinge that can be coupled to a towing vehicle, such as a cart or tractor. Wheel 25 is rotatably mounted to a pair of flanges 26 fixedly mounted to bar 22 and depends therefrom allowing wheel 25 to engage the ground 120 and support frame 21. At the opposite end of the frame, a pair of wheels 28 and 29 is rotatably mounted to frame 21. Wheels 25, 28 and 29 support the vehicle as the vehicle is towed across a field.

A source of ultraviolet light 30 is mounted to frame 21 has a plurality of ultraviolet lamps to shine downwardly against the field. The source of ultraviolet 30 has a housing 31 closed on the top but opened on the bottom to allow the light from the ultraviolet lamps mounted therein to shine downwardly. Housing 31 has a top wall 34 joined to a pair of side walls 35 and 36 extending across the width of the vehicle and joined to a pair of end walls 37 and 38. Walls 35-38 extend angularly downward from the top wall and are fixed to frame 21.

A pair of identical ultraviolet lamp fixtures 32 and 33 is slidably mounted to housing 31 from the opposite sides thereof. End wall 38 has a slot 40 into which lamp fixture 32 is slidable. Likewise, end wall 37 is provided with a slot 41 through which lamp fixture 33 is slidable. Both lamp fixtures 32 and 33 rest atop shelves (not shown) provided within housing 31 to support the fixtures. Each lamp fixture 32 and 33 includes six removable ultraviolet lamps that are removably mounted thereto. The ultraviolet lamps 42 (FIG. 3) are arranged in rows extending lengthwise across the width of the vehicle. In the embodiment shown in FIG. 3, a total of 12 lamps are shown with six parallel lamps extending from one side of the vehicle to the approximate middle of the vehicle whereas the second set of parallel lamps 42 extend from the general middle location of the vehicle to the opposite side of the vehicle. Ultraviolet lamps are commercially available from a variety of lamp manufactures. Conventional male and mating female electrical connectors are provided in housing 31 to connect lamp fixtures 32 and 33 and thus lamps 42 to a source of electrical energy carried on the vehicle. The connectors are automatically electrically connected together by the action of fixtures 32 and 33 being slid into position.

A pair of identical 12 volt, 150 watt DC gel cell batteries 50 and 51 is mounted atop frame 21 and is connected via a conventional inverter 52 to lamps 42. The lamps operate on 115 volt AC with inverter 52 converting the DC power to AC power to energize the lamps.

A conventional generator or engine 53, is mounted atop frame 21 and is connected via inverter 52 to recharge batteries 50 and 51. In addition, inverter 52 may be connected by an auxiliary cord to a stationary source of alternating current, such as available in a building to recharge the batteries when not in use whereas engine 53 may be used to recharge the batteries both when the batteries are in use and not in use.

A brush 60 (FIG. 3) extends across the width of the vehicle and is attached and mounted to frame 21. Brush 60 includes a plurality of downwardly extending bristles to engage the synthetic field fibers to cause the fibers to extend generally vertical allowing the ultraviolet lamps to shine downwardly through the open bottom of housing 31 onto both sides of the synthetic fibers.

Three rows 62, 63 and 64 of downwardly extending tines are aligned to be parallel to each other and extend across the width of the vehicle and are mounted to frame 21. The tines are provided to contact the infill material between the synthetic upstanding fibers to move and turn over the infill material thereby exposing the material to the ultraviolet light. Brush 60 is positioned between the most rearward row 64 of tines and the source of ultraviolet light 30. The brush forms an engager that contacts the synthetic blades prior to the ultraviolet lamps shining thereon. The brush therefore positions the blades on the field to receive the ultraviolet light and destroy any infectious material thereon.

Figure 4:
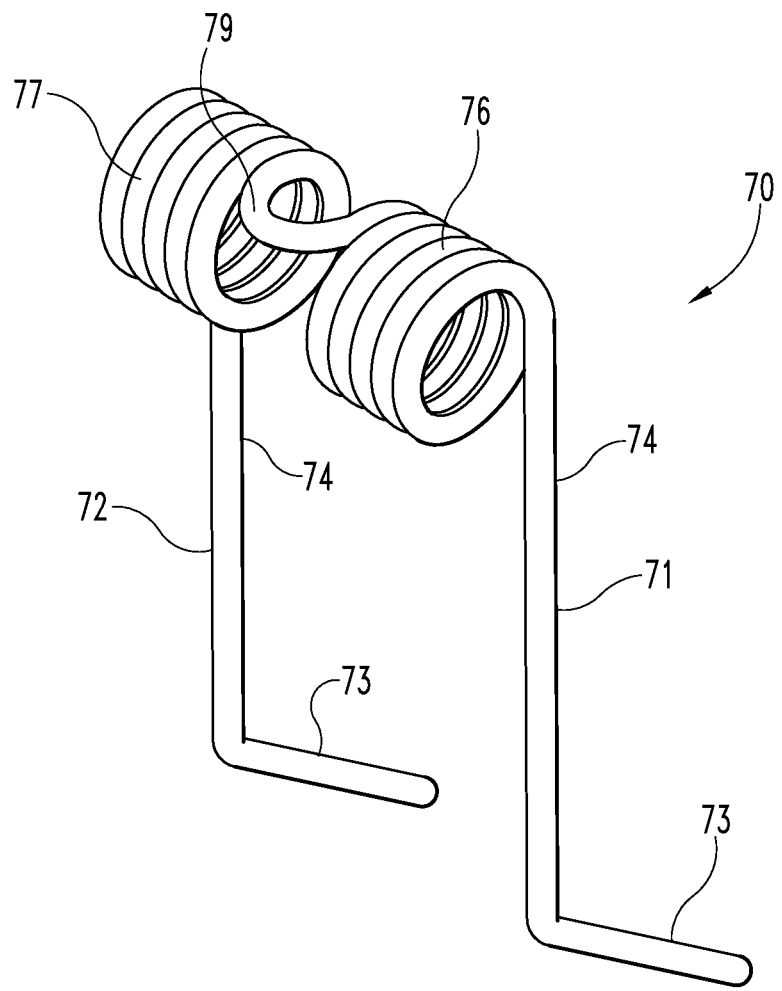
FIG. 4 is an enlarged perspective view of a pair of the tines for mounting to one of the rows of tines.
Figure 5:
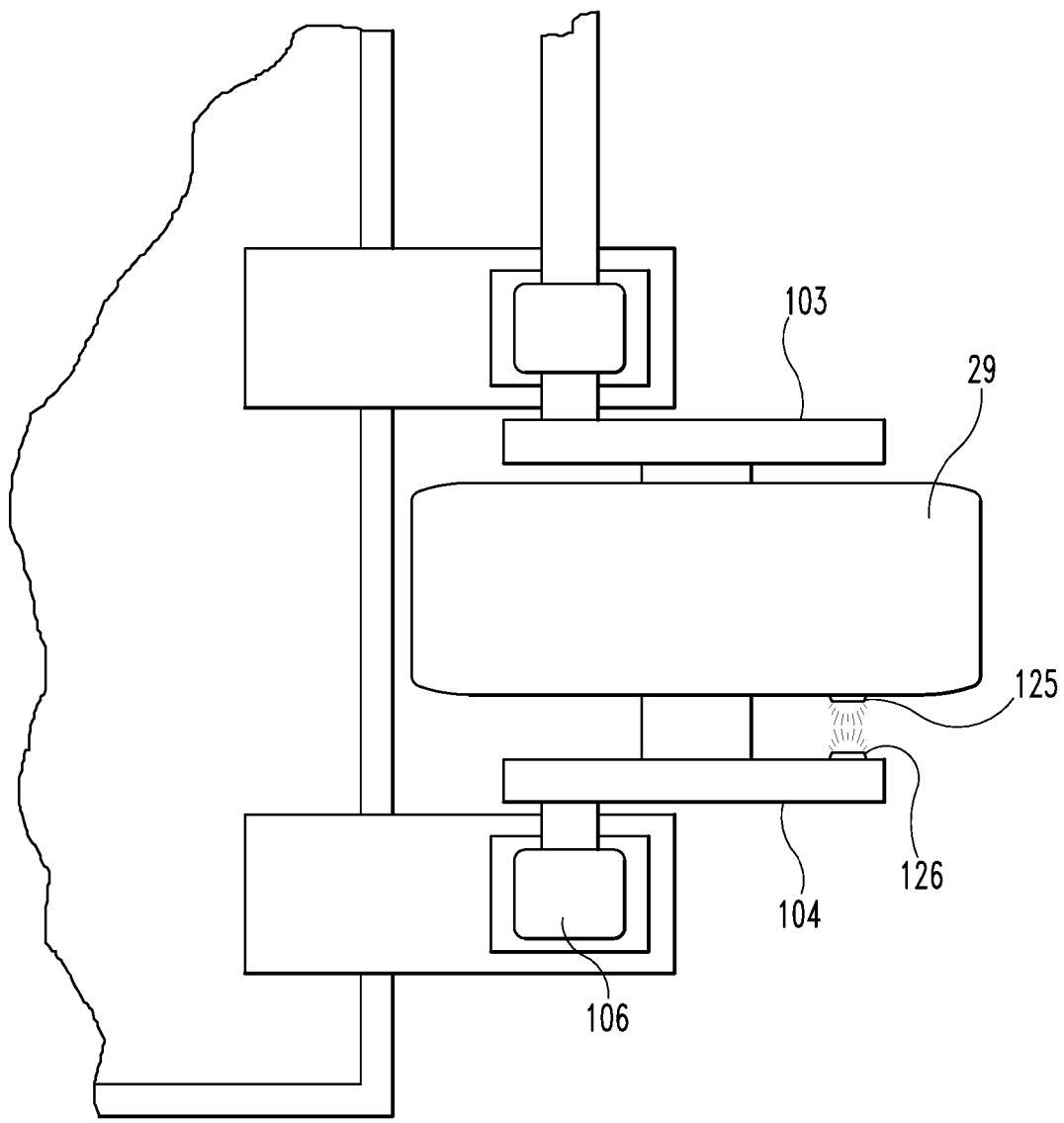
FIG. 5 is an enlarged fragmentary view of rear wheel 29 illustrating the positioning of the infrared sensor to detect stationary movements.
Figure 6:
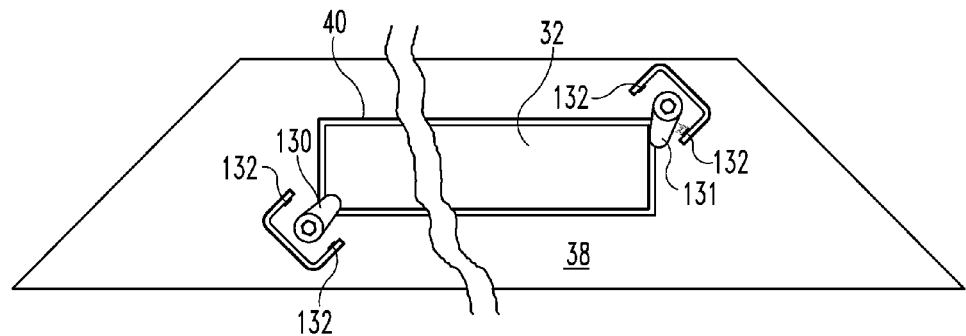
FIG. 6 is an enlarged fragmentary side view looking in the direction of arrows 6-6 of FIG. 2 of light fixture 32 held in place by a pair of cam locks.
Figure 7:
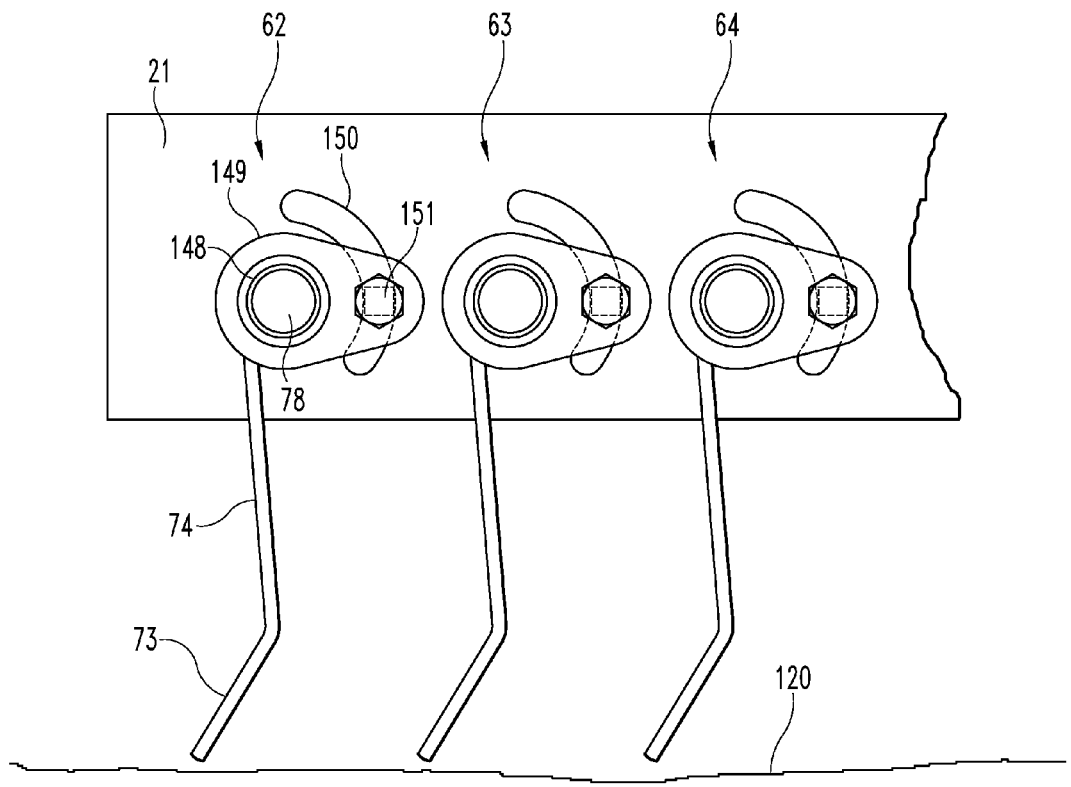
FIG. 7 is an enlarged fragmentary side view of frame 21 illustrating the mounting arrangement of the rows of tines.

Row 62 of tines will now be described it being understood that an identical description applies to tine rows 63 and 64. The tines are grouped in pairs. For example, pair 70 (FIGS. 3 and 4) includes a pair of wire shaped downwardly extending members 71 and 72 having bottom end portions 73 integrally joined to upwardly extending straight portions 74 with the proximal ends 73 (FIG. 1) arranged with respect to straight portions 74 at an approximate angle 75 of 40 degrees. The top end of straight portion 74 of tine 71 is integrally attached to a helically wound portion 76, in turn, integrally joined to a second helically wound portion 77, in turn, integrally joined to the top end of straight portion 74 of tine 72. Tines 71 and 72 are identical in construction.

Helical portions 76 and 77 are mounted to rod 78 (FIG. 1) that extends therethrough. Helical portion 76 and 79 are integrally joined together by a c-shaped middle section 79 (FIG. 4) that rests against a protruding head 80 (FIG. 1) extending outwardly from and fixedly mounted to rod 78. Head 80 extends into c-shaped section 79 thereby limiting movement of tines 71 and 72. As the vehicle moves in a forward direction 81 (FIG. 1), bottom ends 73 of each tine 71 and 72 contact the infill material between the upstanding synthetic fibers causing tines 71 and 72 to pivot backward towards the rear of the vehicle; however, c-shaped portion 79 in conjunction with the helical spring portion 76 and 77 return the tines to their original positions.

A flexible skirt 90 has a top end 91 mounted to frame 21 with the skirt extending down immediately above the field to prevent the ultraviolet light shining outward to an observer standing adjacent the vehicle. An LED light 92 is mounted to the top wall 34 of housing 31 to shine and provide a warning that the ultraviolet lamps are emitting ultraviolet light.

Wheels 28 and 29 are rotatably mounted to a pair of flanges, in turn, mounted to rod 100 that may be rotated to pivot the wheels up and down. For example, a pair of downwardly extending flanges 101 and 102 rotatably receive wheel 28 whereas downwardly extending flanges 103 and 104 rotatably receive wheel 29. The outward facing flanges 101 and 104 are mounted to bearings 106, in turn, fixedly mounted to flanges 107 affixed to frame 21. Rod 100 is rotatably received by bearings 109 mounted atop flanges 110 fixedly mounted to the frame. An actuator 112 (FIG. 1) has a bottom end 113 pivotally mounted to frame 21 and has an extendable rod 114 attached to rod 100 being operable to rotate rod 100. Rod 100 is located off center with respect to the rotational axis of wheels 28 and 29 with the result that rotation of rod 100 causes wheels 28 and 29 to pivot upwardly or downwardly with respect to the supporting surface 120 upon which the vehicle rides.

In operation, when moving the vehicle across supporting surface 120, when it is desired that the tines not contact the supporting surface, rod 114 is extended causing wheels 28 and 29 to pivot and move downwardly thereby lifting frame 21 to the point that the tines do not contact the supporting surface. In the event it is desired that the tines contact supporting surface 120, then rod 114 is retracted causing upward movement of wheels 28 and 29 thereby lowering frame 21 and allowing the bottom portions 73 of the tines to contact supporting surface 120.

The method of destroying the infectious material present on a field having synthetic upstanding blades using the vehicle shown in FIGS. 1-7 includes the step of moving a wheeled vehicle across the field while engaging the blades on the field by the vehicle. A source of ultraviolet light is carried on the vehicle and is positioned to shine the source of ultraviolet light downwardly against the blades to destroy the infectious material. The method includes the additional step of carrying a source of electrical energy on the vehicle to power the ultraviolet light. The engaging step includes the sub-step of brushing the blades to position the blades to receive the ultraviolet light thereby destroying the infectious material. Further, the method includes the additional step of shielding the ultraviolet light to provide safety for an operator of the vehicle by minimizing the visibility of the ultraviolet light from aside the vehicle. The method further includes the step of contacting the loose material between the blades by the vehicle as vehicle is moved across the field to expose the loose material to the ultraviolet light shining downwardly thereon. The step of contacting the loose material includes a sub-step of extending rigid members down from the vehicle and between the blades to move and turn over the loose material. In order to adjust the bottom ends of the tines relative to the field supporting surface, the method includes adjustably raising and lowering the vehicle by a pair of wheels located on the rear of the vehicle to controllably limit contact with the field. In the event the bottom ends of the tines are to be positioned apart form the supporting surface, then the rear wheels are moved downwardly sufficient so as to raise the vehicle frame and position the bottom ends of the tines apart from the supporting surface. On the other hand, if it is desired to control the amount of penetration of the tines into the loose material on the field, then the wheels are raised until the bottom ends of the tines penetrate the desired amount into the loose material. In order to maintain the ultraviolet lamps on the vehicle, the lamps are removably held to allow replacement thereof.

End walls 37 and 38 and side walls 35 and 36 of housing 31 as well as the top wall 34 of the housing provide inner surfaces to reflect the ultraviolet light downwardly. The slanted walls 35-38 are arranged at an angle to allow the ultraviolet light to extend beyond the immediate outline of each lamp.

In certain instances, it is desired to control the amount of ultraviolet light that shines upon the synthetic blades. That is, in the event the vehicle is stationary for a specified duration, then it is desirable to turn off the ultraviolet lamps to prevent the ultraviolet light from shining upon the synthetic blades for an unacceptable duration. To this extent, a commercially available infrared sensor 126 is mounted to flange 104 and is operable to detect movement of target 125 mounted to the mutually facing surface of wheel 29. A timing circuit is provided so that once rotation of wheel 29 stops for a predetermined time, for example 30 seconds, sensor 126 sends a signal to inverter 52 interrupting the flow of electrical energy to the ultraviolet lamps thereby turning the lamps off. As a result, the method disclosed herein includes deactivating the source of ultraviolet light when the vehicle is stationary on the field for a preset time.

In the event light fixtures 32 and 33 become accidentally dislodged from housing 31, micro switches are activated by cam locks normally holding the light fixtures in place to interrupt the flow of electrical energy to the light fixtures. For example, a pair of cam locks 130 and 131 is eccentrically mounted to end wall 38 and are designed to extend inwardly over the corners of light fixture 32. In the event the cam locks rotate allowing the light fixture 32 to move outwardly, then the cam locks contact conventional micro switches 132, in turn, connected to inverter 52 interrupting the flow of electrical energy to light fixtures and ultraviolet lamps. Cam locks identical to locks 130 and 131 along with switches identical to switches 133 are provided on wall 33 to hold fixture 33 and control the flow of electrical energy to fixture 33.

Some synthetic fields do not have crumb rubber (infill material) between the synthetic blade fibers. Thus, the main body of the supporting rod for each row of tines 62-64 may be rotated to rotate the tines upwardly apart from the field. For example, the ultraviolet lamp on the vehicle may be used to kill fungus on the blades of a standard golf green; however, it is imperative that the tines not extend down and engage the dirt between the non-synthetic blades of grass.

Each row of tines 62-64 (FIG. 3) includes a rod rotatably mounted at its opposite ends to the side walls of main frame 21 or interior walls, in turn, mounted to frame 21. Each rod includes a flange integrally secured thereto at each opposite end of the rod. The flange has a teardrop shape with the flange mounted eccentrically with respect to the rod. For example, rod 78 includes an end 148 (FIG. 7) integrally attached to one end of teardrop shape flange 149 positioned against the side wall of frame 21. The opposite end of flange 149 includes a slot 150 through which fastener 151 extends. Flange 149 can be pivoted about the longitudinal axis of rod 78 with fastener 151 moving between the opposite extremes of slot 150 to position the bottom ends 73 of the tines apart from supporting surface 120 or position the tips of bottom tine ends 73 into the supporting surface at a controlled distance.

Many variations are contemplated and included in the present invention. For example, the embodiment shown in the drawing has a single brush extending across the width of the vehicle between the tines and the UV lamps. It is also possible to position a separate brush between rows 62 and 63 and another brush between rows 63 and 64 in order to increase the repositioning of the synthetic turf fibers and infill material therebetween.

Another variation of the present invention includes adding standard louvers to housing 31 in order to allow heat within the housing and generated by the UV lamps to escape upwardly. The UV lamps may take many different configurations. In the embodiment shown in the drawing, each lamp fixture 32 and 33 is approximately 36 inches wide by 36 inches in length and 6 inches in height. Each lamp fixture is shown as having six UV lamps removably mounted thereto; however, it is to be understood that at the present invention includes more than or less than two light fixtures and more than or less than six UV lamps for each lamp fixture.

Referring now more particularly to FIGS. 8-14, there is shown the preferred embodiment of the mobile vehicle 200 having a main frame 201 with a general rectangular configuration. A tow bar 202 has a proximal end pivotally mounted by hinge 203 (FIG. 9) about a horizontal axis to main frame 201 to enable the tow bar distal end 204 to move up and down and sideways for attachment to the towing vehicle. A pair of conventional front wheels 205 (FIG. 10) are each rotatably mounted by conventional brackets about a horizontal axis with the brackets then being pivotable about a vertical axis allowing the wheels to rotate and swivel in a conventional manner as the frame is towed across a field. A pair of rear wheels 206 are rotatably mounted each about a horizontal axis by brackets fixedly attached to main frame 201 to enable the rear wheel to rotate as the main frame is towed. The rear wheels do not swivel. Likewise, frame 201 is not moved vertically with respect to the front wheels or rear wheels since the actuator 112 (FIG. 1) provided in the alternate embodiment of the mobile vehicle is not included in the preferred embodiment of the mobile vehicle 200 shown in FIG. 8.

A source of electrical energy or generator 207 (FIG. 8) is mounted atop main frame 201 by conventional brackets and is normally enclosed by housing 208 having an edge portion 209 hingedly secured to main frame 201. Housing 208 is shown in the upward position thereby revealing source 207; however, it is to be understood that in normal operation housing 208 is pivoted downward to conceal the source of electrical energy 207. A plurality of louvers are provided in the side walls of housing 208 to enable air to circulate around the source of electrical energy.

A plurality of ultraviolet lamps are removably mounted to frame 201 and operate on 115 volt AC in one version of the preferred embodiment of the mobile vehicle. The source of electrical energy 207 includes a gasoline operated internal combustion engine 210 having a gasoline storage tank 211 provided in a combination unit, such as available from Honda under Model Nos. EU1000i or EU2000i. The electrical output of the internal combustion engine is 12 volts DC used to power status light bulbs located on the main frame and also capable to recharge batteries 213. An inverter 212 is mounted to the main frame and is operable to convert 12 volts DC from the engine to 115 volts AC supplied to the ultraviolet lamps. In the event it is desired to operate the mobile sterilization unit in a quieter mode, the batteries 213, preferably gel cell batteries, are provided which, in turn, are electrically connected to inverter 212 for purposes of converting the battery direct current output to 115 volt AC supplied to the ultraviolet lamps. In order to recharge batteries 213, engine 209 may be activated thereby connecting the direct current output of the engine to batteries 213 for the recharging thereof. Alternatively, the batteries may be recharged by an external source other than the engine.

In order to control the spacing of the ultraviolet lamps with respect to the turf field, the lamps are removably mounted in a lamp housing 220 (FIG. 8) which is movable vertically by operation of mechanism 221. The mechanism 221 includes a pair of upstanding brackets 222 (FIG. 8a) having bottom ends fixedly mounted to frame 201 with the top ends of members 222 having an internally threaded bar 223 through which worm drive or gear 224 threadedly extends. The outer end 225 of the worm gear is attached to a hand crank 226 whereas the opposite end of worm gear 224 is connected to a pair of spaced apart members 227 extending rearwardly. The forward ends of members 227 are connected together by plate 228 in which the rearward most end of worm gear 224 is held captive. Thus, rotation of worm gear 224 results in members 227 moving forward or rearward along a horizontal axis as the crank 226 is rotated.

Rod 230 (FIG. 8) has opposite ends 231 and 232 rotatably mounted by brackets 233, in turn, rotatably attached to frame 201. A pair of upstanding arms 234 have bottom ends fixedly mounted to rod 230 and top ends connected together by fastener 235 extending through a slot in the rearward ends of members 227. Thus, rotation of the crank 226 in a first direction causes members 227 to move rearwardly which causes arms 234 to pivot in a counterclockwise direction as viewed in FIG. 8 thereby rotating rod 230.

A second rod 240 has opposite ends 241 rotatably mounted in downwardly extending brackets 242 supporting the rod 240 and allowing the rod to rotate about a horizontally extending axis. A second pair of arms 244 have bottom ends fixedly attached to rod 240 and top ends secured by fastener 245 to the rearward end of connecting members 246. The forward end of members 246 are attached by fastener 235 to arms 234. As a result, rotation of worm gear 224 causes coordinated movement of arms 234 and 244 and thus coordinated rotation of rods 230 and 240. When the crank is rotated to move members 227 rearwardly, arms 234 and 244 are caused to rotate along with rods 230 and 240 in a counterclockwise direction as viewed in FIG. 8.

A forward pair of downwardly extending slotted brackets 250 have top ends fixedly attached to frame 201 with the two brackets 250 located on the opposite sides of frame 201. Likewise, a rearward pair of slotted brackets 251 have top ends fixedly attached to frame 201 with the two brackets 251 located on the opposite sides of frame 201. A front pair of links 252 have forward ends connected to the opposite ends of rod 230 and move therewith. Likewise, a pair of rearward links 254 are connected to the opposite ends of rod 240 and move therewith. Links 252 are located on the opposite sides of frame 201. Likewise, links 254 are located on the opposite sides of frame 201. The most rearward ends 255 of links 252 extend through the vertical slot of brackets 250 and are connected to lamp housing 220. Likewise, the rearward ends 256 of the pair of links 254 extend through the vertical slot of brackets 251 and are attached to the rearward portion of the lamp housing. Rotation of crank arm 226 in a first direction causes worm gear 224 to rotate thereby resulting in rearward movement of members 227 and 246 with the resultant counterclockwise movement of rods 230 and 240, in turn, causing the forward pair of links 252 and the pair of rearward links 254 to pivot with the opposite ends of rods 230 and 240. The rearward ends 255 and 256 of links 252 and links 254 thereby move downwardly in the slots of brackets 250 and 251 spacing lamp housing 220 and the ultraviolet lamps mounted therein apart from the turf field a first distance. The slots may be designed so that when the rearward ends of links 252 and 254 are located at the bottom of the slots, the ultraviolet lamps are spaced apart the optimum distance from the field to achieve maximum sterilization results. Excellent results have been obtained by positioning the lamps two inches above the sports field. Rotation of the crank handle in a second direction opposite of the first direction causes worm gear 224 to rotate thereby moving members 227 and 246 forwardly resulting in clockwise motion as viewed in FIG. 8 of rods 230 and 240. As a result, the rearward ends 255 and 256 of links 252 and 254 move upwardly in the slots of brackets 250 and 251 raising the lamp housing and ultraviolet lamps contained therein from the turf field a distance greater than the optimum distance to enable transportation of the mobile vehicle when the ultraviolet lamps are not activated.

When the mobile unit is being used to sterilize the turf field, the lamp housing and ultraviolet lamps are in the lower position. A plurality of rollers 260 (FIG. 8) are rotatably mounted to the lamp housing to protect the ultraviolet lamps when in the lower sterilization position. The rollers are rotatably mounted and extend slightly beneath the lamp housing bottom edge and automatically cause the lamp housing to move upward in the event the rollers encounter a foreign object such as a rock. The rollers do not normally contact the ground or field unless a sudden rise the ground or field is encountered. In the embodiment shown in FIG. 10, three such rollers are mounted to the lamp housing on the front portion of the lamp housing and three rollers are rotatably mounted to the rear portion of the lamp housing.

Lamp housing 220 (FIG. 8) is a four sided rectangular frame having an open top and an open bottom. The housing includes a pair of side walls 271 and 272 (FIG. 10) joined to end walls 273 and 274. A ledge 276 (FIG. 12) is integrally attached to rear wall 274 and extends between side walls 271 and 272. A second inwardly extending ledge 277 is attached to front wall 273 and extends between the side walls 271 and 272. Two lamp modules 290 and 291 (FIG. 8) are inserted into housing 220 from atop of the lamp housing and rest therein on ledges 276 and 277.

Figure 14:
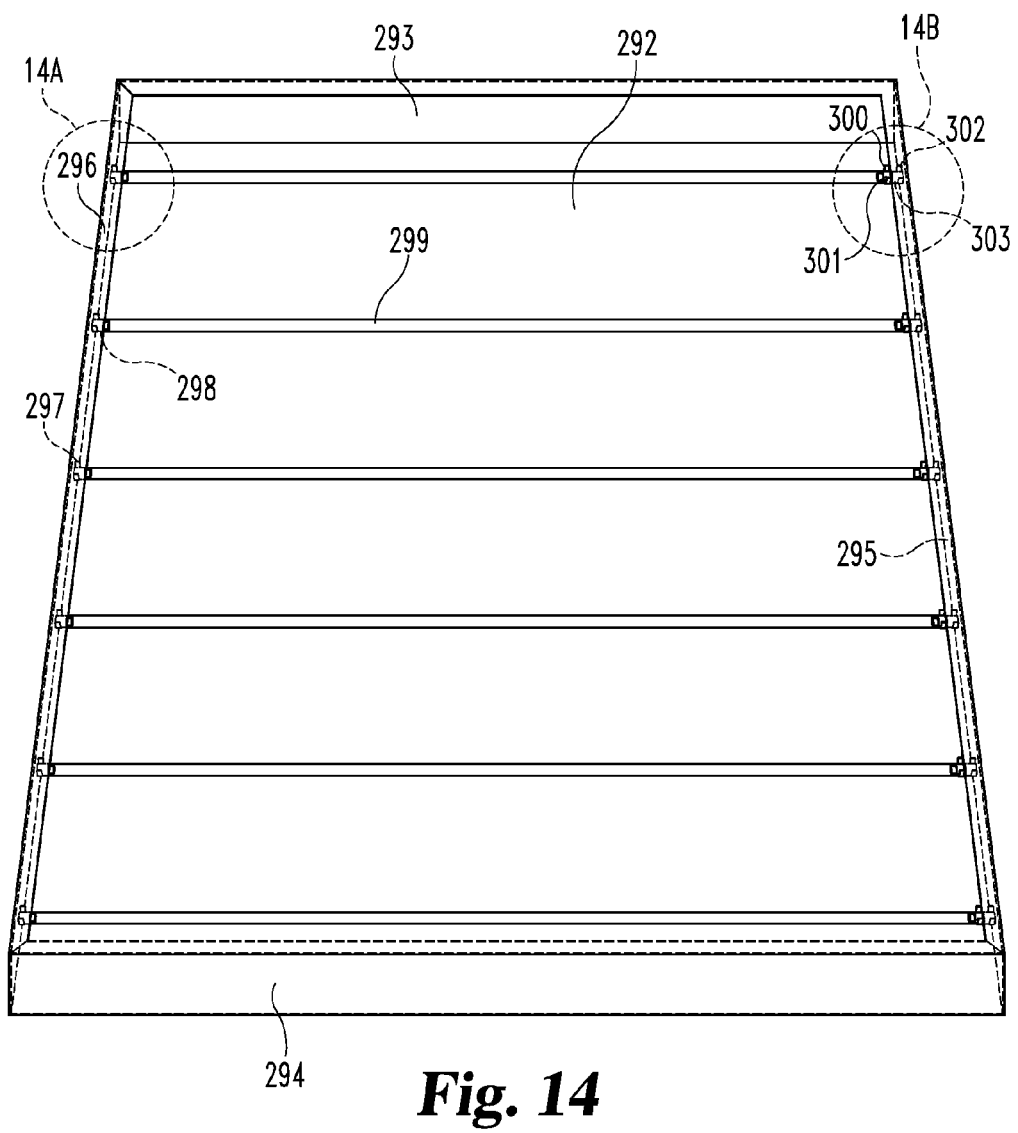
FIG. 14 is an enlarged bottom perspective view of a lamp module with ultraviolet lamps mounted therein.
Figure 14A:
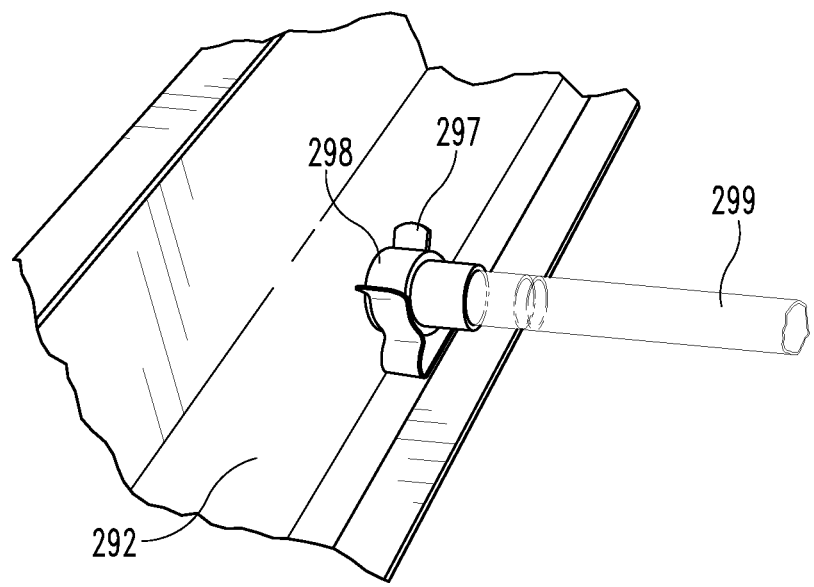
FIG. 14a is an enlarged fragmentary view of the distal end of a ultraviolet lamp held by a clip shown in the enclosed circle 14a of FIG. 14.
Figure 14B:
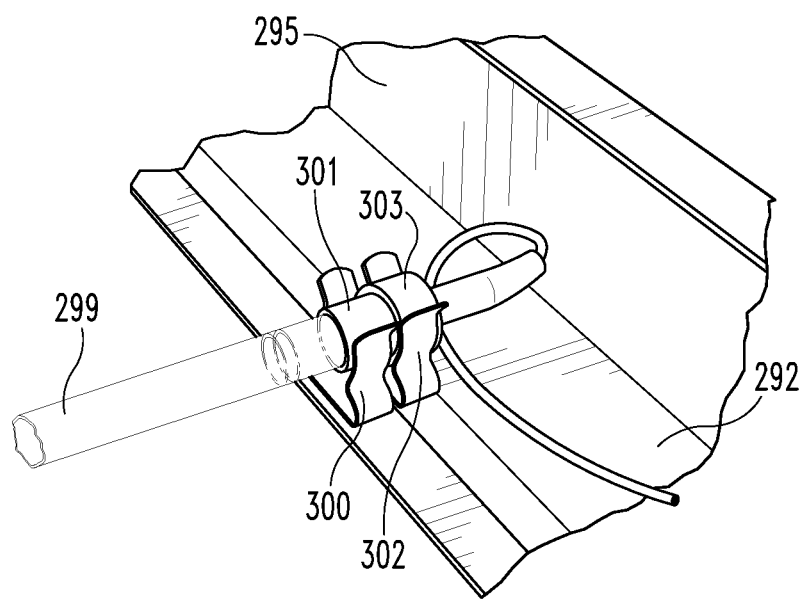
FIG. 14b is an enlarged fragmentary view of the proximal end of a ultraviolet lamp held by a clip along with the attached electrical connector shown in the enclosed circle 14b of FIG. 14.

Lamp module 290 (FIGS. 13 and 14) will now be described it being understood that an identical description applies to lamp module 291. Lamp module 290 is five sided container having a closed top wall 292 joined to a pair of end walls 293 and 294 and a pair of side walls 295 and 296. Four handles 297 are attached to top wall 292 and project thereabove. The bottom of lamp module is open to allow the ultraviolet lamps contained therein to shine downwardly. In the version of the lamp module depicted in FIG. 13, a total of six ultraviolet lamps are removably mounted therein and are arranged in parallel rows extending in a direction across the width of frame 201. The inside surface that faces downwardly of top wall 292 (FIG. 14) is highly reflective in order to reflect downward energy from the ultraviolet lamps towards the turf field. Fixedly mounted to top wall 292 and facing downwardly are six clips 297 having spring biased arms to releasably hold ends 298 of lamps 299. Six additional clips 300 identical to clips 297 are mounted to wall 292 to releasably hold the opposite ends 301 of the ultraviolet lamps. A third set of clips 302 identical to clips 297 are mounted to top wall 292 immediately adjacent to wall 295 to hold a plurality of commercially available electrical connectors 303. Clips 302 which hold the connectors 303 cooperatively support with clips 300 the proximal ends 301 of the lamps. Connectors 303 may have female sockets into which the outwardly projecting pins of lamp ends 301 project. Likewise, ends 301 of the ultraviolet lamps may have inwardly projecting sockets to electrically receive outwardly projecting pins of electrical connectors 303. All six of the connectors 303 are then connected by conventional wiring to the source of electrical energy. FIGS. 14a and 14b illustrate clips 297, 300 and 302 holding lamp 299 and connector 303.

Figure 12:
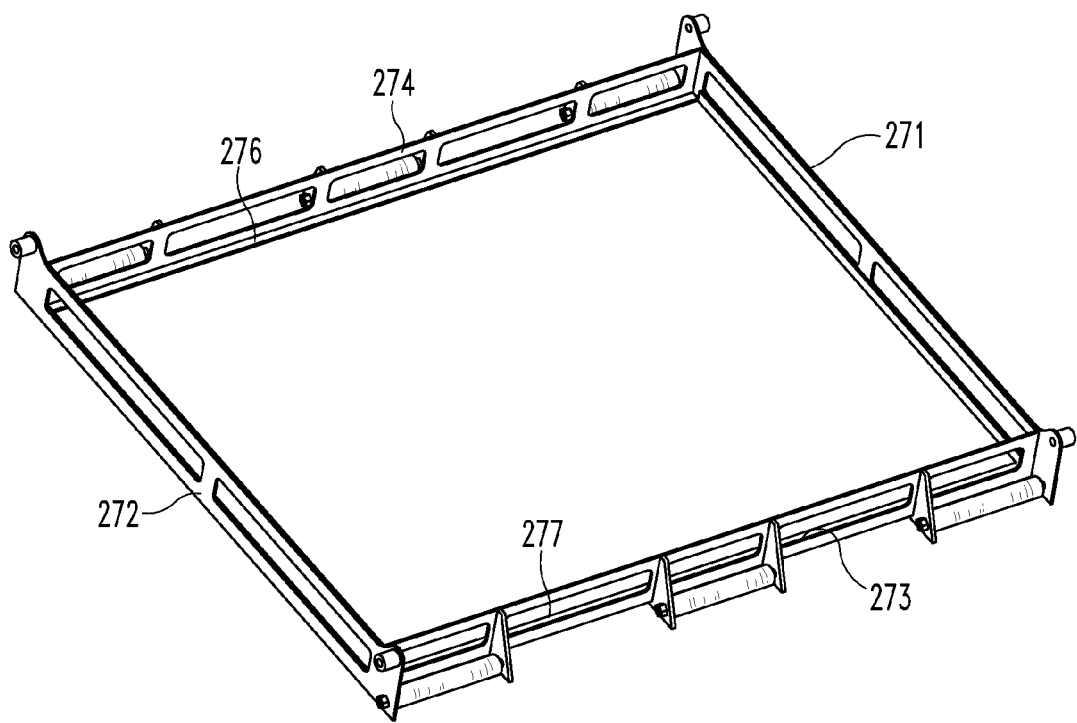
FIG. 12 is an enlarged top perspective view of the lamp housing.
Figure 13:
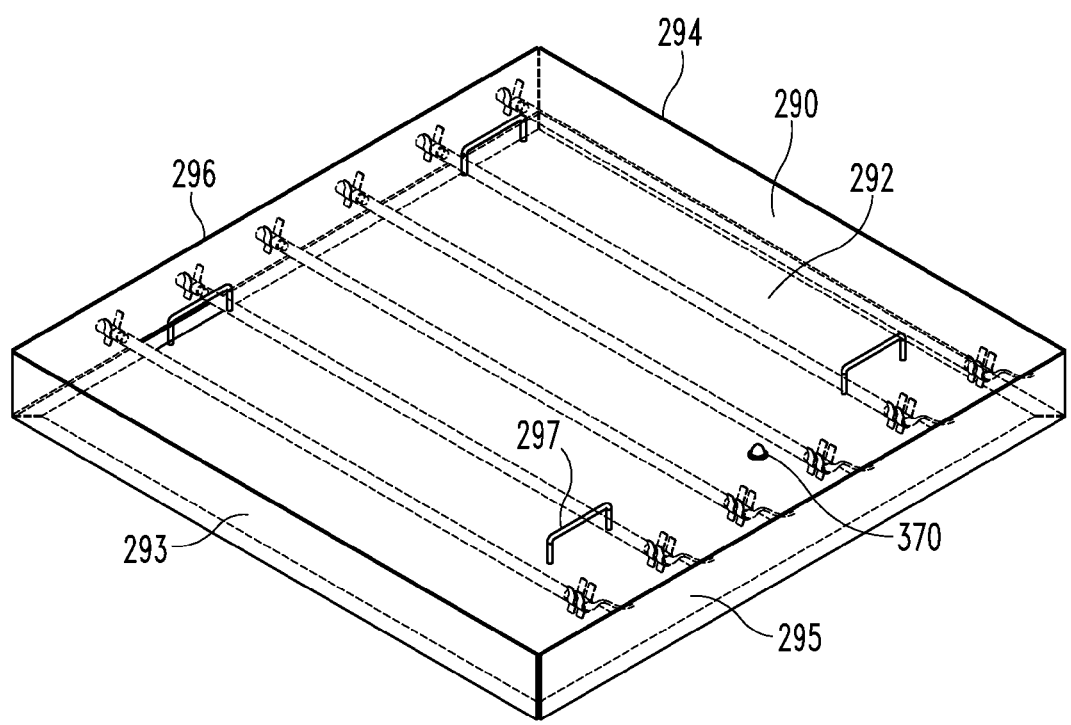
FIG. 13 is an enlarged top perspective view of a lamp module.

In order to install or remove lamp modules 290 and 291, the lamp housing 220 is lowered to its lowest position by cranking handle 226 and then slipping the lamp modules over and into the lamp housing 220 from the sides of frame 201. Depending upon the spacing, links 254 may be disassembled in order to slip each lamp module through the gap between frame 201 and lamp housing 220 until each lamp module is immediately over the lamp housing and then dropping into place resting atop ledges 276 and 277 (FIG. 12). Thus, lamp module 290 may be inserted from the right as viewed in FIG. 8 through gap 306 between frame 201 and the lamp housing whereas the second lamp module 291 is inserted through a similar gap on the opposite side of the frame. Handles 297 are provided to facilitate holding the lamp module as is inserted or removed from the lamp housing.

Vehicle 200 includes the downwardly extending brushes 60 (FIG. 10) previously described for vehicle 20 (FIG. 3). Further, the rows 62, 63 and 64 of tines extend downwardly from vehicle 200 (FIG. 10) previously described for vehicle 20 (FIG. 3). The locations and functions of the brushes and tines are the same for vehicle 200 as described for vehicle 20. Since vehicle 200 does not include actuator 112 which raises the frame of vehicle 20 thereby also raising the brushes and tines for transportation during the non-sterilization condition, the brushes and tines of vehicle 200 may be mounted on a secondary frame pivotally mounted to frame 201 of vehicle 200. The secondary frame maybe pivoted upwardly thereby disengaging the brushes and tines when it is desired to move vehicle 200 without the brushes and tines engaging the turf field. The secondary frame may be releasably locked in the upward, non-use position by means of a removably pin extendable into frame 201 and the secondary frame. Certain fields do not include loose material between the blades and thus, the blades and tines may be stored in the upward position.

Figure 8:
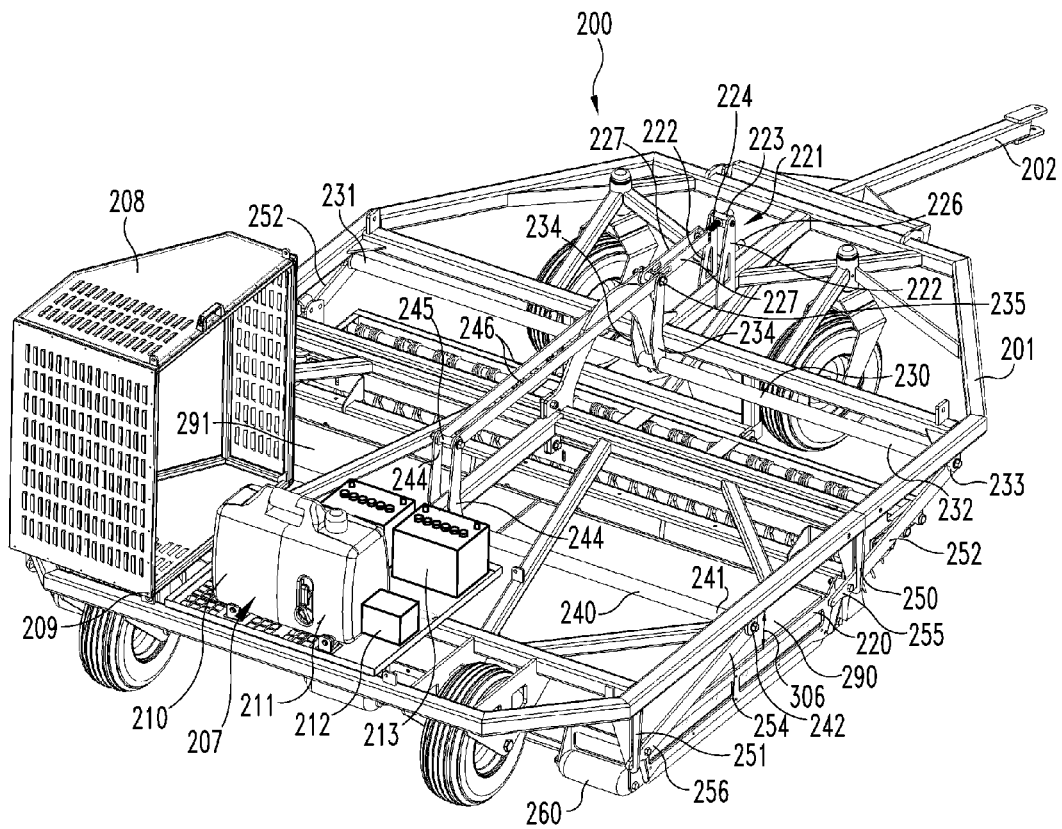
FIG. 8 is a rear perspective view of the preferred embodiment of the vehicle incorporating the present invention.
Figure 8A:
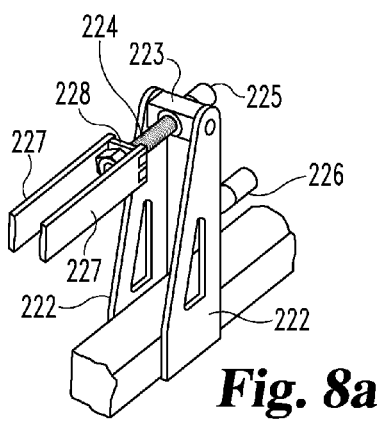
FIG. 8a is a fragmentary rear perspective view of the crank mechanism.
Figure 9:
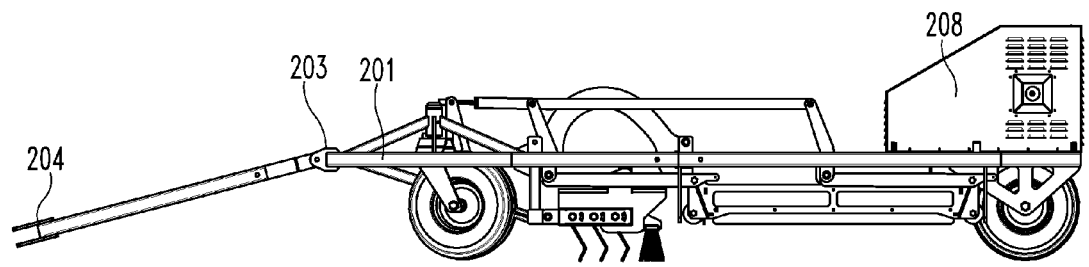
FIG. 9 is a left side view of the vehicle of FIG. 8.
Figure 10:
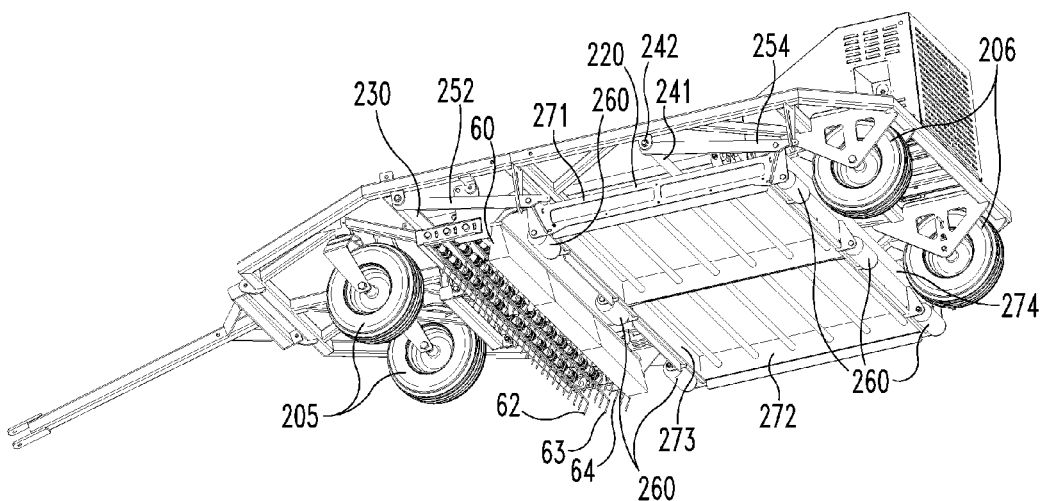
FIG. 10 is a bottom perspective view of the vehicle of FIG. 9.
Figure 11:
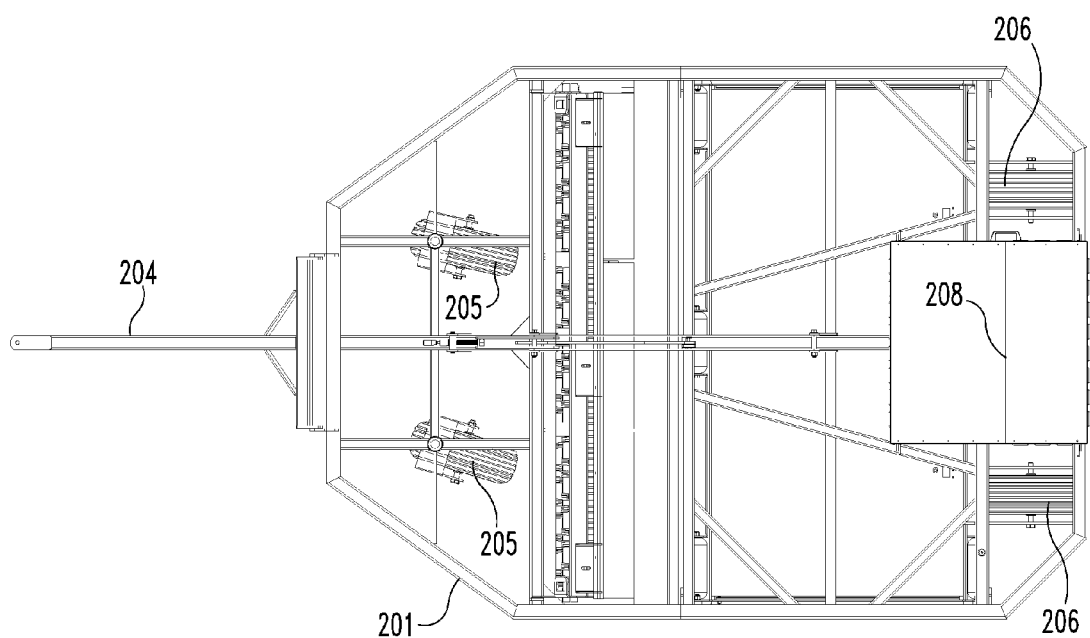
FIG. 11 is a top view of the vehicle of FIG. 8.

Skirt 90 described for vehicle 20 and illustrated in FIG. 1 is also provided for vehicle 200 but has been deleted from FIG. 8 in order to more fully illustrate the structure of the vehicle. Such a skirt is attached to frame 201 and extends downwardly around the light housing 220 to limit a person from seeing the ultraviolet light shinning down from the ultraviolet lamps.

Figure 15:
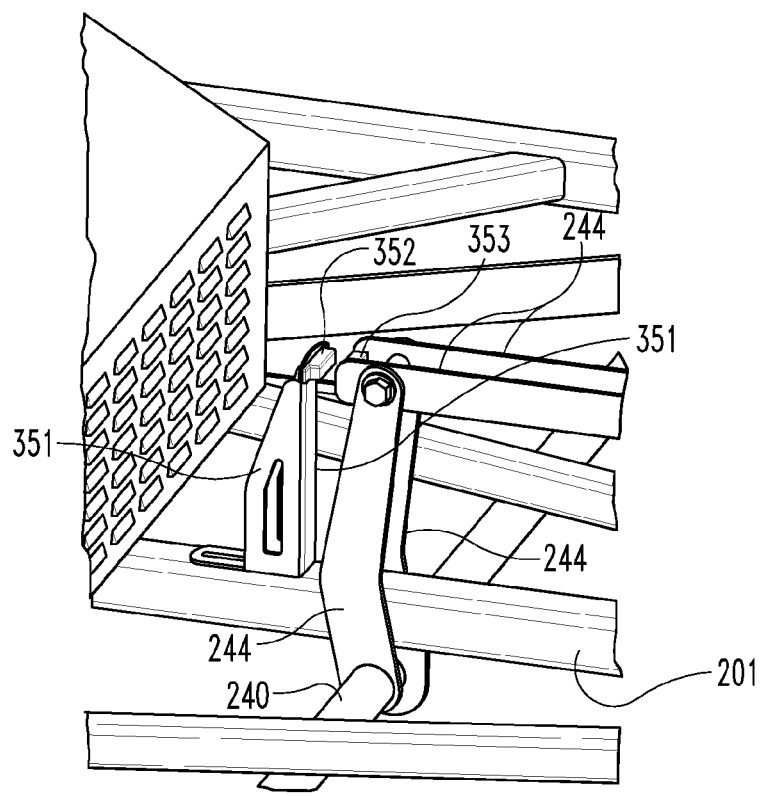
FIG. 15 is a fragmentary view of the vehicle illustrating a safety switch for allowing flow of electrical energy to the ultraviolet lamps only if the light housing is in the downward position.

A safety switch (FIG. 15) is mounted to frame 201 to prevent the flow of electrical energy to the ultraviolet lamps unless the light housing 220 is positioned at the most bottom position spacing the ultraviolet lamps the required distance to sterilize the field. The switch includes a pair of arms 351 having bottom ends slidably mounted to frame 201 and top ends with a bumper 352 mounted thereto and aligned with a corresponding bumper 353 mounted to the top ends of arms 244. When the light housing 220 is in the upward position, bumpers 352 and 353 are spaced apart positioning the forwardly spring biased switch 350 in the forward position illustrated in FIG. 15. As arms 244 move rearwardly pivoting rod 240 counterclockwise as viewed in FIG. 15, links 254 pivot counterclockwise as viewed in FIG. 8 forcing the light housing to the bottom position while bumper 353 contacts bumper 352 moving arms 351 rearwardly and closing the switch allowing electrical energy to flow from the source of electrical energy to the ultraviolet lamps.

Figure 16:
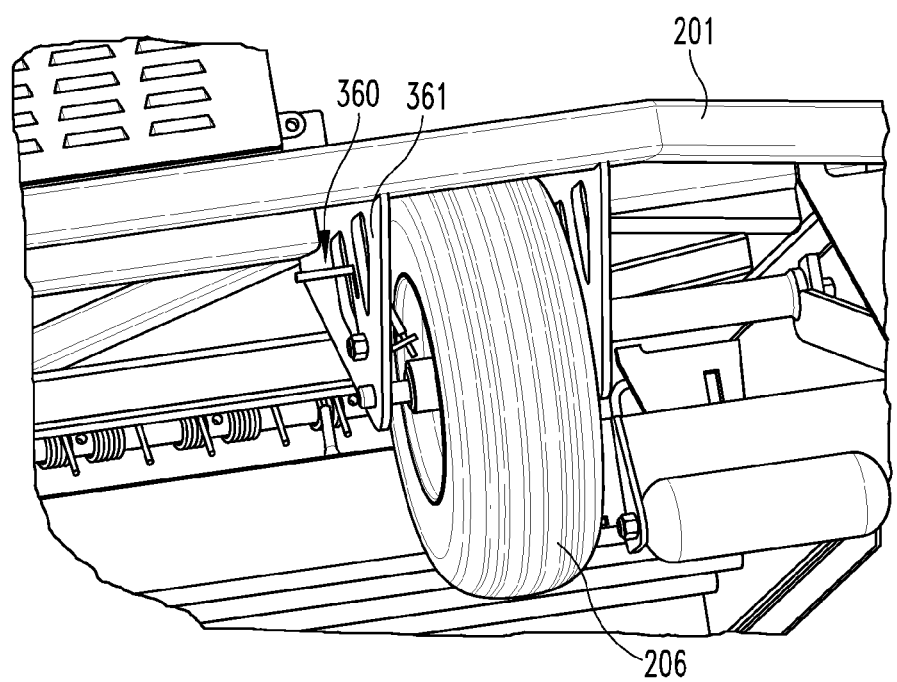
FIG. 16 is a fragmentary rear view of the vehicle illustrating a motion sensor for detecting motion of a rear wheel.

A second safety switch 360 (FIG. 16) is mounted to wheel mounting bracket 361. Switch 360 is a standard commercially available motion sensor and monitors motion of wheel 206. The switch is operable to interrupt the flow of electrical energy from the source of electrical energy to the ultraviolet lamps in the event the wheels have not moved for more than a specified time, for example fifteen or thirty seconds. Switch 360 prevents the turf from degradation in the event the vehicle is stationary for a more than a specified time with the lamps in the on position. A kill switch, not shown, is in series with the wiring from the source of electrical energy to the lamps to allow immediate interruption of the flow of electrical energy to the lamps when depressed for use in an emergency. Likewise, a reset switch is provided to reactivate the flow.

Each lamp module 290 and 291 include an indicator light 370 (FIG. 13) connected in series with the wiring to the lamp connectors to indicate when the lamps are activated in the on position.

The method of minimizing the infectious material of the blades of a synthetic or living turf field includes providing vehicle 200 with the downwardly shining ultraviolet lamps and spacing the lamps apart from the fields a first distance. Excellent results have been obtained by spacing the lamps apart from the field a distance of 2 inches to 3 inches. In such a case, the vehicle was moved across the field at an approximate speed of 8 to 10 miles per hour. Best results have been achieved by moving the vehicle across the field in a first direction, for example, across the width (side to side) of the field and also across the field in a second direction different from the first direction, for example, across the length (end to end) of the field and also across the field in a third direction different from both the first direction and second direction, for example, diagonally (corner to corner) across the field while the lamps shine ultraviolet energy against the blades of the turf field. By moving the vehicle across the width, length and diagonal of the field, the lamps shine ultraviolet energy against different portions of the blades of the field increasing the exposure of the infectious material to the ultraviolet energy. In addition, the method includes the step of extending downwardly an engager, such as the brush and tines disclosed herein, which contact the blades and the loose material between the blades of the field thereby repositioning the blades and loose material to receive the ultraviolet light as the vehicle is moved in different direction across the field.

The ultraviolet lamps used with the vehicle and method described herein are commercially available. For example, such lamps are manufactured by American Ultraviolet Company, Lebanon, Ind. under Model Number GTL 36 GG. The lamps may be Teflon coated to provided extra safety in the event the lamp breaks. Excellent results have been obtained with forty watt lamps. The ballast units used with the ultraviolet lamps may be mounted within the lamp modules.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, the vehicle and method described for sterilizing turf fields or sports fields it being understood that such includes not only soccer/football/lacrosse/baseball fields but also golf courses and any field having artificial or living turf susceptible to contamination.

What is claimed is:

1. A vehicle to move across a sports field having blades to destroy infectious material on said field comprising:
    a frame:
    a wheel rotatably mounted on said frame and extending downwardly to support said frame as said frame is moved across a sports field;
    a source of ultraviolet light mounted on said frame and having ultraviolet lamps to shine downwardly against the field, said lamps have proximal ends and distal ends both of which are mounted to said frame;
    a source of electrical energy mounted on said frame and connected to said proximal ends of said ultraviolet lamps;
    connectors connecting said proximal ends of said ultraviolet lamps to said source of electrical energy;
    first mounts on said frame and removably receiving said proximal ends of said ultraviolet lamps and supporting said lamps on said frame;
    second mounts on said frame and removably receiving said distal ends of said ultraviolet lamps and supporting said lamps on said frame; and
    a lamp housing movably mounted to said frame;
    a mechanism to raise and lower said housing to position said lamps the desired distance over the field; and,
    lamp modules removably mounted in said lamp housing and having said ultraviolet lamps removably mounted therein; and
    said lamp housing includes an open top through which said lamp modules may be installed or removed from said housing, said mechanism includes a hand operated crank attached to a worm drive in turn linked to said housing to raise and lower said lamp housing.

2. The vehicle of claim 1 wherein said mechanism is operable to position said lamps two inches to three inches above the sports field.

3. A vehicle to move across a sports field having blades to destroy infectious material on said field comprising:
    a frame:
    a wheel rotatably mounted on said frame and extending downwardly to support said frame as said frame is moved across a sports field;
    a source of ultraviolet light mounted on said frame and having ultraviolet lamps to shine downwardly against the field, said lamps have proximal ends and distal ends both of which are mounted to said frame;
    a source of electrical energy mounted on said frame and connected to said proximal ends of said ultraviolet lamps;
    connectors connecting said proximal ends of said ultraviolet lamps to said source of electrical energy;
    first mounts on said frame and removably receiving said proximal ends of said ultraviolet lamps and supporting said lamps on said frame; and,
    second mounts on said frame and removably receiving said distal ends of said ultraviolet lamps and supporting said lamps on said frame; and
    wherein said source of electrical energy includes an engine mounted on said frame to provide electrical energy to said lamps and a plurality of batteries to provide electrical energy to said lamps when said engine is not being used.

4. A vehicle to move across a sports field to minimize infectious material thereon with the field having blades of artificial grass with loose material between the blades comprising:
    a frame;
    a lamp housing removably mounted to said frame and having an open bottom;
    ultraviolet lamps removably mounted on said lamp housing and positioned to shine downwardly through said open bottom of said housing against a sports field, said lamps have proximal ends and distal ends;
    a mechanism on said frame to raise and lower said lamp housing to position said lamps a first distance from said sports field;
    a plurality of tines mounted on said frame having bottom ends contactable with loose material on the sports field, said tines mounted forward of said ultraviolet lamps to move and turn over the loose material as said frame is moved across the field to receive ultraviolet light to minimize infectious material thereon;

a brush mounted on said frame and extending downwardly engageable with the blades to position the blades to receive ultraviolet light to minimize infectious material thereon;
a source of electrical energy mounted on said frame and coupled to said proximal ends of said ultraviolet lamps to power same;
connectors connecting said proximal ends of said lamps to said source of electrical energy;
clamps mounted on said frame and releasably engageable with said connectors and proximal ends and distal ends of said lamps to support said lamps on said frame;

a wheel rotatably mounted to said frame and engageable with said field to support said frame above the field; and wherein said ultraviolet lamps are arranged in rows extending in a direction across the width of said frame to shine on the blades and loose material as the vehicle is moved across the field; and, said source of electrical energy includes an internal combustion engine mounted on said frame being electrically connected to said lamps.

5. The vehicle of claim 4 and further comprising:

a skirt depending from said frame to limit flow of ultraviolet energy from the sides of the vehicle.

* * * * *